(12) United States Patent
Denman

(10) Patent No.: US 8,297,577 B1
(45) Date of Patent: *Oct. 30, 2012

(54) FOLDING URINE SPECIMEN CUP HOLDER

(76) Inventor: Tabetha M. Denman, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/373,038

(22) Filed: Nov. 3, 2011

Related U.S. Application Data

(62) Division of application No. 12/378,373, filed on Feb. 17, 2009, now Pat. No. 8,079,562.

(51) Int. Cl.
A47K 1/08 (2006.01)
(52) U.S. Cl. .................. 248/311.2; 248/201; 4/144.1
(58) Field of Classification Search ............... 248/311.1, 248/175; 4/144.1, 559, 445; 141/372
See application file for complete search history.

(56) References Cited

U.S. PATENT DOCUMENTS

| 2,167,795 | A | * | 8/1939 | Bentz | ............ 4/574.1 |
|---|---|---|---|---|---|
| 3,571,817 | A | | 3/1971 | Gosnell | |
| 4,203,169 | A | | 5/1980 | Dale | |
| 5,146,637 | A | | 9/1992 | Bressler et al. | |
| D489,453 | S | | 5/2004 | Sapyta | |
| 7,011,634 | B2 | | 3/2006 | Paasch et al. | |

* cited by examiner

Primary Examiner — Amy J Sterling
(74) Attorney, Agent, or Firm — George L. Williamson

(57) ABSTRACT

A foldable urine collection device which comprises a pair of wire members having first and second opposed ends and having an upwardly disposed urine collection cup intermediate said first and second ends so that the urine collection cup is generally centrally disposed within a toilet bowl for use by a user wherein the first and second ends of the wire frame connect to opposing rims of the toilet bowl so as to secure the device therein. Also shown is an intermediately disposed net having a plurality of flexible fingers disposed so as to capture the collection cup therein in a manner so that a plurality of sizes of collection cups can be captured with the flexible fingers. The flexible fingers secure the cup within the urine collection device.

7 Claims, 4 Drawing Sheets

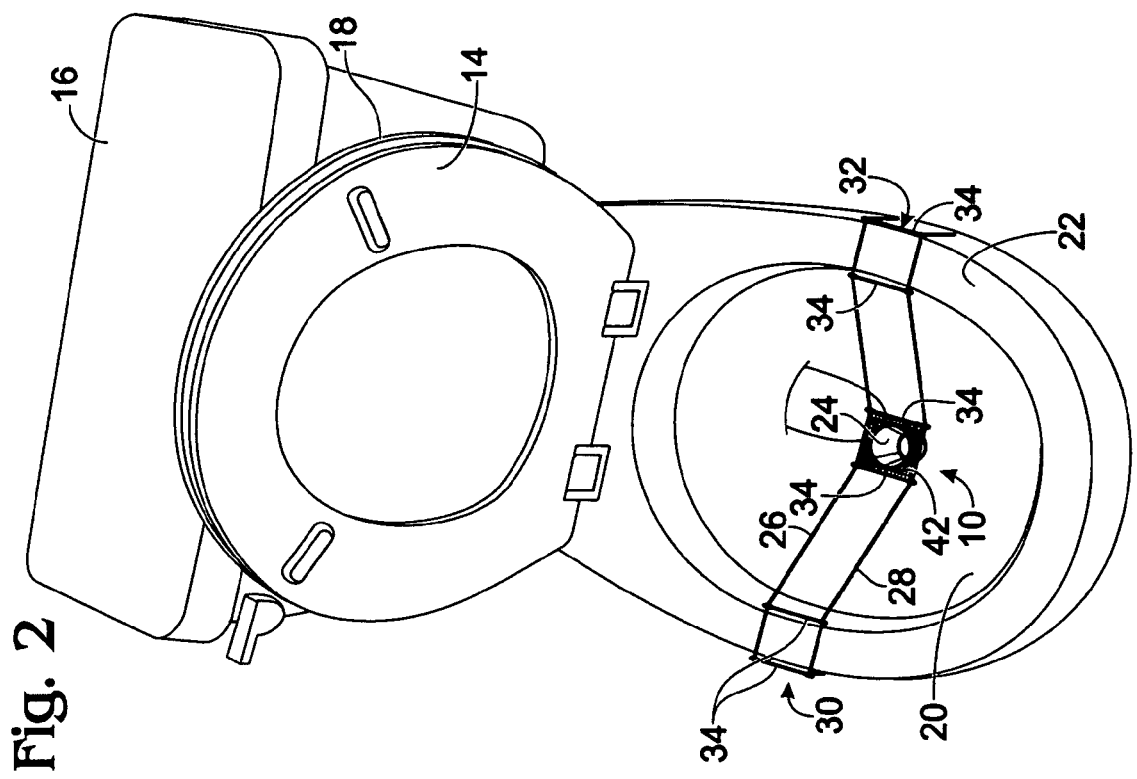
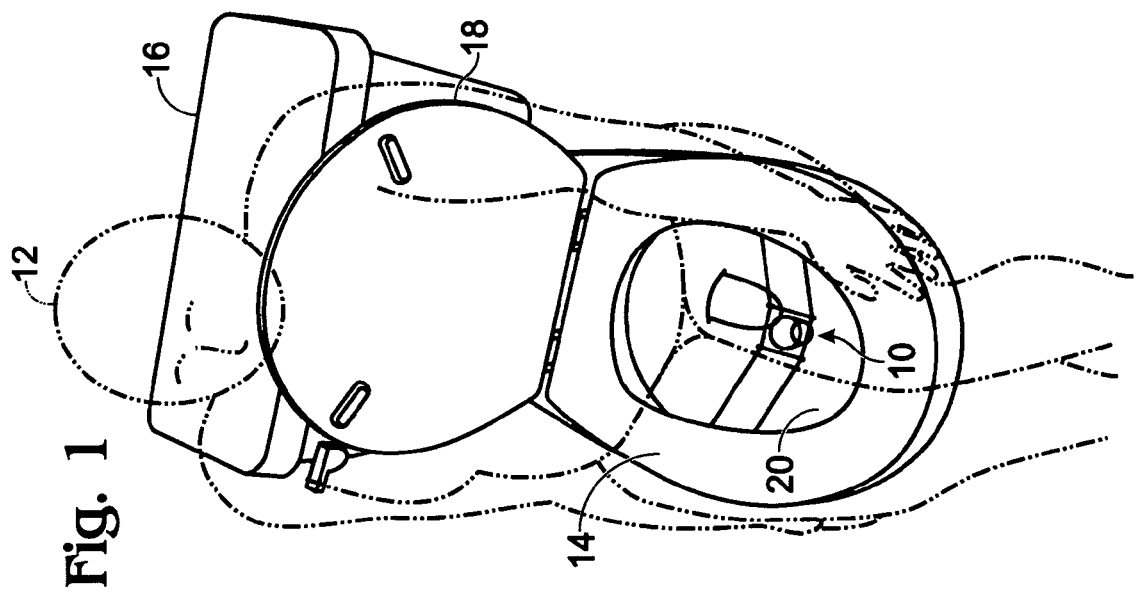

FOLDING URINE SPECIMEN CUP HOLDER

RELATED APPLICATION

This is a Divisional Application of U.S. patent application Ser. No. 12/378,373 filed on Feb. 17, 2009 now U.S. Pat. No. 8,079,562.

BACKGROUND OF THE INVENTION

1. Field of the Invention

The present invention relates generally to medical devices and, more particularly, is concerned with a urine collection device.

2. Description of the Related Art

Urine collection devices have been described in the related art, however, none of the related art devices disclose the unique features of the present invention.

In U.S. Pat. No. 4,203,169 dated May 20, 1980, Dale disclosed a urine collection device. In U.S. Pat. No. 5,146,637 dated Sep. 15, 1992, Bressler, et al., disclosed a female urine collection apparatus. In U.S. Pat. No. 3,571,817 dated Mar. 23, 1971, Gosnell disclosed a urine specimen collector.

While these urine collection devices may be suitable for the purposes for which they were designed, they would not be as suitable for the purposes of the present invention as hereinafter described.

SUMMARY OF THE PRESENT INVENTION

The present invention discloses a foldable/collapsible urine collection device which comprises a pair of parallel wire or the like frame members having first and second opposed ends and having an upwardly disposed urine collection cup intermediate said first and second ends so that the urine collection cup is generally centrally disposed within a toilet bowl for use by a user wherein the first and second ends of the wire frame connect to opposing rims of the toilet bowl so as to secure the device therein. Also shown is an intermediately disposed net having a plurality of flexible fingers disposed so as to capture the collection cup therein in a manner so that a plurality of sizes of collection cups can be captured with the flexible fingers. The flexible fingers secure the cup within the urine collection device.

An object of the present invention is to provide a sanitary means for urine collection. A further object of the present invention is to provide a urine collection device which can be foldably/collapsibly packaged for shipment or storage in a flat package and easily removed therefrom and unfolded for use. A further object of the present invention is to provide a urine collection device which is disposable. A further object of the present invention is to provide a hands free urine collection device which can be used with a variety of sizes of collection cups.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which:

FIG. 1 is a perspective view of the present invention shown in operative connection.

FIG. 2 is a perspective view of the present invention shown in operative connection.

LIST OF REFERENCE NUMERALS

Figure 3:
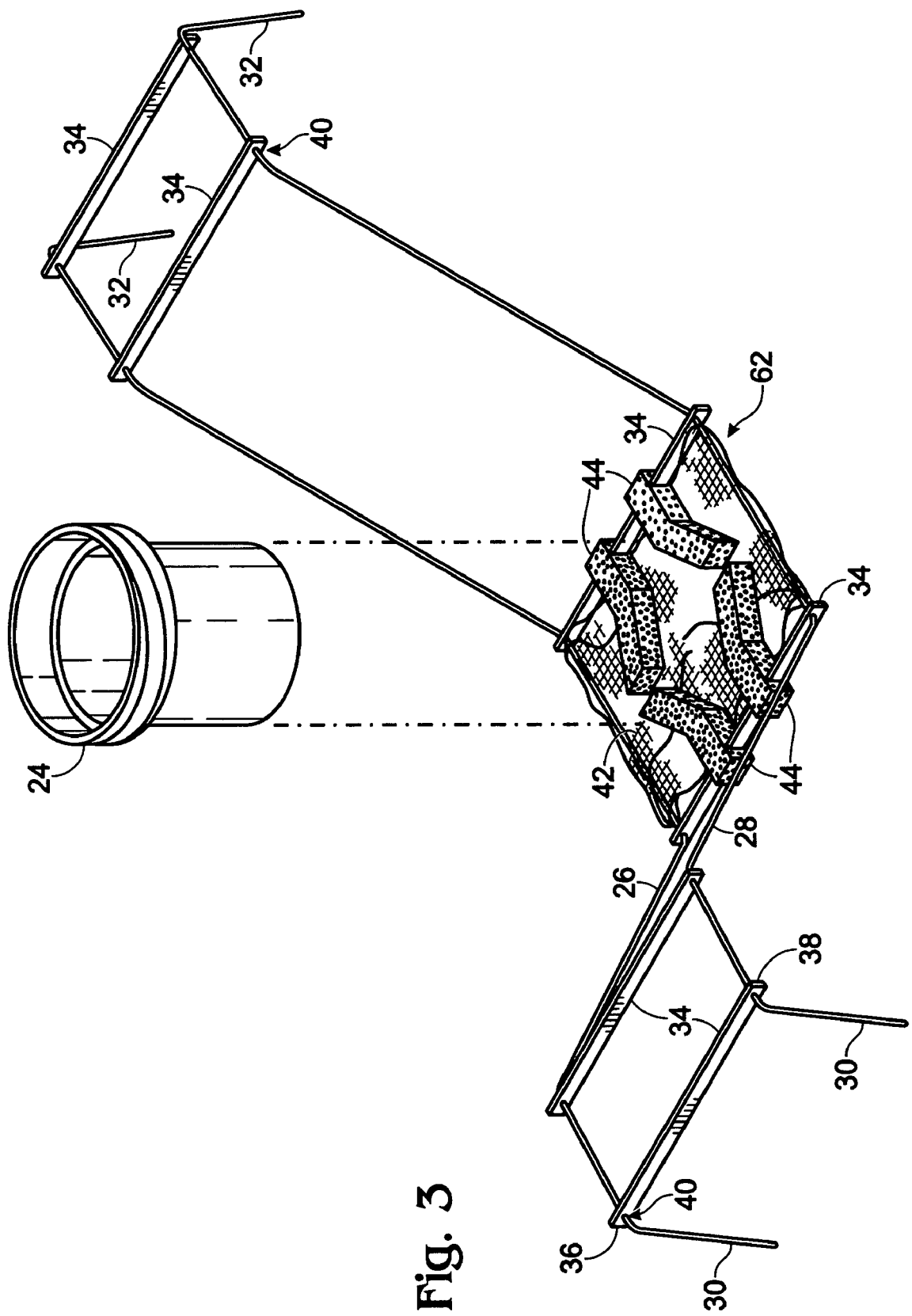
FIG. 3 is a perspective view of the present invention.

With regard to reference numerals used, the following numbering is used throughout the drawings.

10 present invention
12 user
14 toilet seat
16 toilet
18 toilet lid
20 toilet bowl
22 toilet rim
24 cup
26 frame member
28 frame member
30 first end
32 second end
34 cross member
36 first end
38 second end
40 aperture
42 net
44 flexible fingers
46 flat position
48 partially raised position
50 fully raised position
52 bend in finger
54 first end
56 second end
58 grasping point
60 grasping point
62 front

DETAILED DESCRIPTION OF THE PREFERRED EMBODIMENT

The following discussion describes in detail at least one embodiment of the present invention. This discussion should not be construed, however, as limiting the present invention to the particular embodiments described herein since practitioners skilled in the art will recognize numerous other embodiments as well. For a definition of the complete scope of the invention the reader is directed to the appended claims. FIGS. 1 through 7 illustrate the present invention wherein a urine collection device is disclosed.

Turning to FIG. 1, therein is shown the present invention 10 being substantially centrally disposed inside the bowl 20 of toilet 16 wherein a user 12 is sitting on the seat 14 of the toilet having the toilet lid 18 in a raised position.

Turning to FIG. 2, therein is shown the present invention 10 being substantially centrally disposed in the interior of the toilet bowl 20 of a toilet 16 wherein the seat 14 and lid 18 are in a raised position. The present invention 10 has a centrally disposed cup 24 which is placed within netting material 42 in generally the middle of a pair of parallel wire, plastic or the like frame members 26, 28 having opposite ends 30, 32 and multiple cross members 34. It can be seen that the ends 30, 32 of the frame members 26, 28 are downwardly disposed on opposite sides of the outside edge of the rim 22 of the toilet bowl 20 so as to secure the present invention 10 to the rim.

Figure 4:
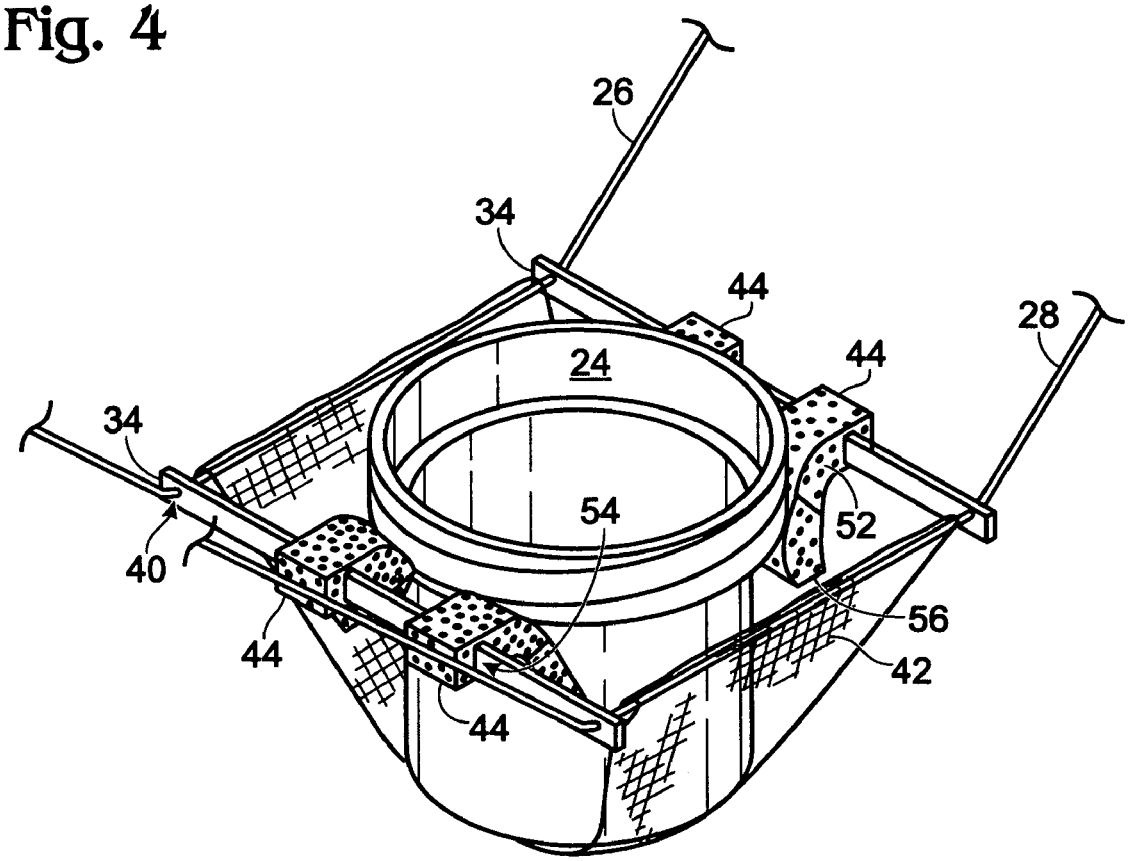
FIG. 4 is a perspective view of portions of the present invention.

Turning to FIGS. 3 and 4, therein is shown the present invention 10 having a cup 24 disposed intermediate the ends 30, 32 of a pair of substantially parallel frame members 26, 28 which are expected to be made of wire, plastic, wood or the like. The wire frame members having a plurality of cross members 34 each having a first and second end 36, 38 which is adapted for being rotatably connected to frame members 26, 28 using an aperture 40 which is provided on each end of cross member 34 so that the frame members 26, 28 can rotate inside the aperture 40 of the cross members 34 and thereby easily rotate from a folded to unfolded configuration. Also shown are means for receiving the cup 24 comprising a flexible netting material 42 disposed intermediate the ends 30, 32 of the frame members 26, 28; and, also shown are a plurality of flexible fingers 44 which netting and fingers capture the cup 24 therein so as to allow a variety of sizes of cups to be used with the present invention 10. Fingers 44 are flexible and bend as shown at 52 so as to be conformed to the shape and size of the cup as the cup 24 is inserted in between the fingers. Fingers 44 are expected to be made of flexible material or rubber-like material or the like and frictionally capture cup 24. Net 42 is flexible, slightly elastic so as to form a sock-like receptacle under the fingers 44 to assist in capturing the cup 24 therein. Net 42 is expected to be made of cloth or plastomeric material or the like. Fingers 44 have one end at 54 adapted for being disposed on (e.g., having an aperture therein) cross-member 34 and a second end 56 which frictionally engages the exterior of cup 24. Also shown is the general "V" shaped profile of the present invention 10 when viewed from the front 62.

Figure 7:
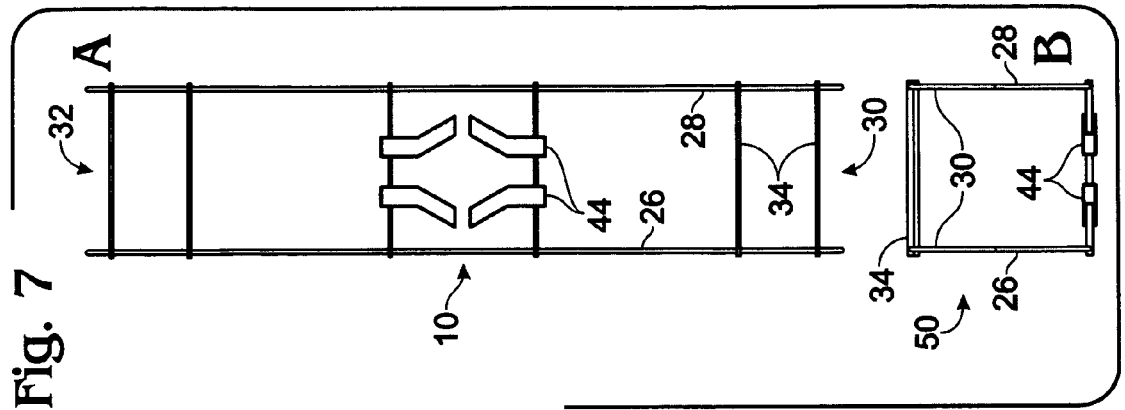
FIGS. 7A and B is a plan view along with an end view, respectively, of the present invention.
Figure 6:
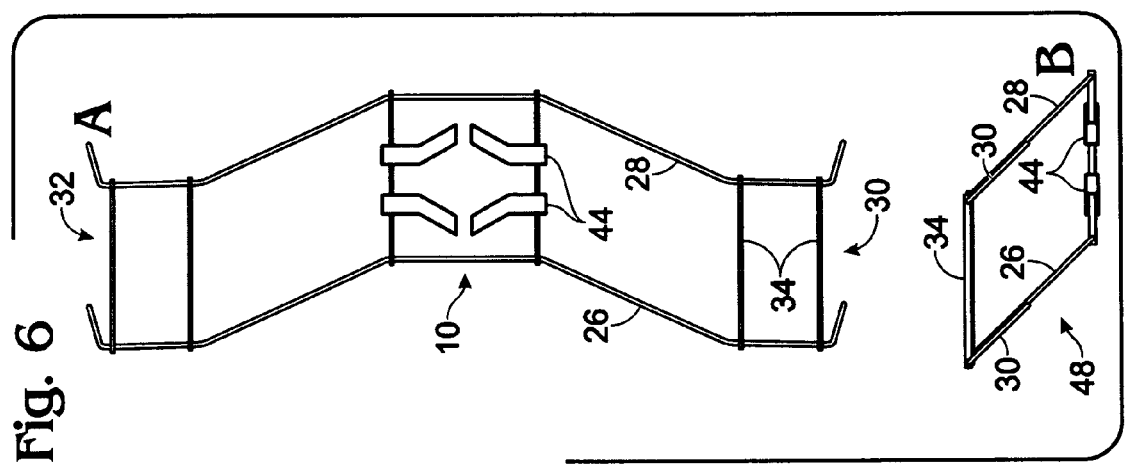
FIGS. 6A and 6B is a plan view along with an end view, respectively, of the present invention.
Figure 5:
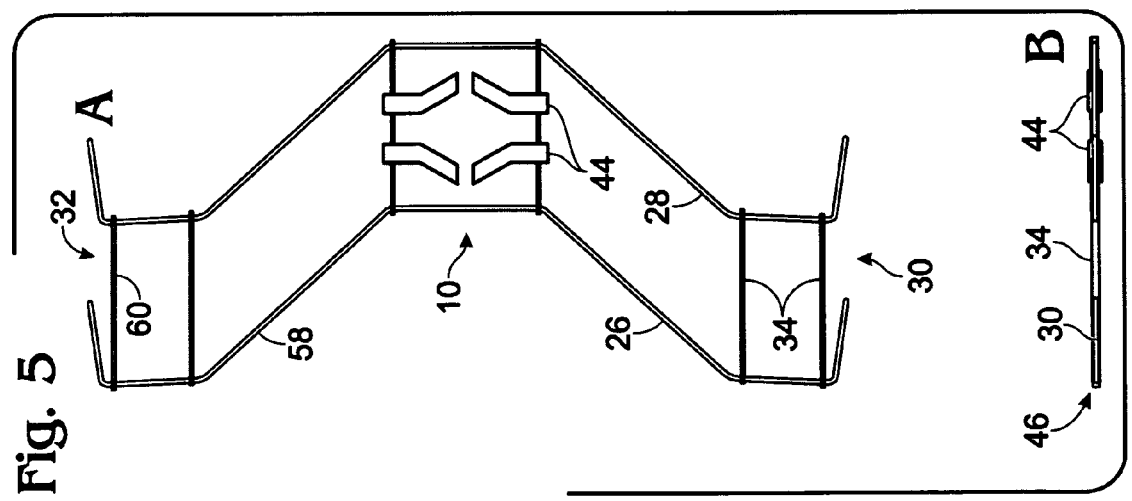
FIGS. 5A and 5B is a plan view along with an end view, respectively, of the present invention.

The steps of unfolding the present invention 10 from the folded to the unfolded position are shown in FIGS. 5 through 7.

Turning to FIGS. 5A and 5B, therein is shown the present invention 10 in a folded position as it would appear in a packaged position. In this position, the present invention 10 is flat and can be very compactly packaged and stored so as to save storage space and shipping costs in route from the manufacturer or distributor to the point of use. Also shown on FIG. 5B is the end profile at 46 showing the present invention in a folded or flat position. Also shown on FIGS. 5A and 5B are the arms 26, 28 along with cross members 34 and ends 30, 32 along with the flexible fingers 44 and grasping points 58, 60 which will be further explained in the following description.

Turning to FIGS. 6A and 6B, therein is shown the present invention 10 in a semi-folded position as it would appear after removal from the package. Also shown on FIG. 6B is the end profile at 48 showing the present invention in a semi-folded position. Also shown on FIGS. 6A and 6B are the arms 26, 28 along with cross members 34 and ends 30, 32 along with the flexible fingers 44.

Turning to FIGS. 7A and 7B, therein is shown the present invention 10 in an unfolded position as it would appear after removal from the package. In this position, the present invention 10 is unfolded and ready for placement on the toilet bowl as previously shown in FIG. 2. Also shown on FIG. 7A is the end profile at 50 showing the present invention in an unfolded position. Also shown on FIGS. 7A and 7B are the arms 26, 28 along with cross members 34 and ends 30, 32 along with the flexible fingers 44.

By way of additional general explanation, the operation/use of the present invention 10 follows. After initially removing the unit 10 from the package it has a profile as shown at 46 of FIG. 5B. By way of example, the user may then unfold the unit 10 by grasping frame member 26 with the left hand at approximately point 58 as shown on FIG. 5A and with the right hand grasping cross-member 34 at approximately point 60 a shown on FIG. 5A and rotating the cross member and frame member 28 about the frame member 26. This will unfold the unit 10 into the profile shown at 50 in FIG. 7B preparing it for placement across the toilet unit 20. This will also demonstrate the general "V" shaped profile of the present invention 10 when viewed from the front as is apparent in FIG. 3. It will be apparent to a user that the present invention 10 can be unfolded by being grasped and/or rotated or otherwise manipulated at numerous points other than 58, 60 of FIG. 5A as stated above.

Next, lift the toilet seat 14 if it is not already in the up position. Place the unit 10 across the rim 22 of the toilet 16 from side-to-side. Place any size urine collection cup 24 in the holder, i.e., netting 42 and fingers 44. Lower the toilet seat 14. Some aiming may be required to obtain a urine sample in cup 24. After the urine sample is obtained, carefully remove the cup 24 and give it to the clinician/hospital assistant. Next, lift the toilet seat 14. Remove the unit 10 by grasping and lifting up on each end 30, 32 of the unit. Dispose of the unit 10 in the proper collection unit.

I claim:

1. An apparatus for holding a urine specimen cup for collecting a urine sample from a user while the user is seated on a toilet, the toilet having a seat, a toilet bowl and a rim, the rim having an outer edge, comprising:
   a) first and second parallel frame members, each said frame member having first and second ends, wherein each said frame member has a downwardly disposed portion on said first and second ends to permit the downwardly disposed portion to be proximate the outer edge of the rim of the toilet bowl;
   b) a plurality of cross members connecting said frame members, each said cross member having first and second ends wherein said first end of said cross member is adapted to be rotatably connected to a corresponding said first frame member and said second end of said cross member is adapted to be rotatably connected to a corresponding said second frame member;
   c) wherein said first and second frame members can be moved from a first folded position to a second unfolded position; and,
   d) means for receiving the urine specimen cup whereby the urine specimen cup is oriented in a position for collecting the urine sample from the user.

2. The apparatus of claim 1, wherein each said first and second ends of each said cross member has an aperture therein, wherein each said aperture is proximate each said end of each said cross member, wherein each said corresponding parallel frame member passes through one said aperture of each said cross member.

3. The apparatus of claim 1, wherein said means for receiving the urine specimen cup further comprises netting material disposed on said first and second frame members for capturing the urine specimen cup therein.

4. The apparatus of claim 3, wherein said means for receiving the urine specimen cup further comprises a plurality of flexible fingers disposed proximate said netting material for capturing the urine specimen cup therein.

5. The apparatus of claim 4, wherein each said flexible finger is disposed on a cross member.

6. The apparatus of claim 1, wherein various sizes of urine specimen cups may be used with the apparatus.

7. The apparatus of claim 1, wherein said frame members have generally the shape of a "V" when viewed from the front in said second unfolded position.

* * * * *